(12) United States Patent
Berger Sharp et al.

(10) Patent No.: US 7,674,058 B2
(45) Date of Patent: Mar. 9, 2010

(54) DISPOSABLE WIPE WITH LIQUID STORAGE AND APPLICATION SYSTEM

(75) Inventors: Cecelia M. Berger Sharp, Atlanta, GA (US); Michael S. Brunner, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 818 days.

(21) Appl. No.: 11/215,812

(22) Filed: Aug. 30, 2005

(65) Prior Publication Data

US 2007/0045135 A1    Mar. 1, 2007

(51) Int. Cl.
*A46B 5/04*    (2006.01)
(52) U.S. Cl. ............................... 401/7; 401/132
(58) Field of Classification Search ............... 401/132, 401/133, 134, 7, 8, 196, 205, 201
See application file for complete search history.

(56) References Cited

U.S. PATENT DOCUMENTS

| | | | |
|---|---|---|---|
| 1,896,941 A | 2/1933 | Cohen | |
| 2,041,262 A | 5/1936 | Ness | |
| 2,076,681 A | 4/1937 | Steinmayer | |
| 2,122,482 A | 7/1938 | Marr et al. | |
| 2,179,614 A | 11/1939 | Cohen | |
| 2,265,329 A * | 12/1941 | Wachs | 401/7 |
| 2,599,191 A | 6/1952 | Meunier | |
| 2,646,796 A | 7/1953 | Scholl | |
| 2,673,365 A | 3/1954 | Moor, Jr. | |
| 2,790,982 A * | 5/1957 | Schneider | 401/7 |
| 2,882,528 A | 4/1959 | Tassie | |
| 2,925,605 A | 2/1960 | Wheeler | |
| 2,966,691 A | 1/1961 | Cameron | |
| 3,070,102 A | 12/1962 | MacDonald | |
| 3,124,824 A | 3/1964 | Lutz | |
| 3,263,681 A | 8/1966 | Nechtow et al. | |
| 3,280,420 A | 10/1966 | Wanzenberg | |
| 3,298,507 A | 1/1967 | Micciche | |
| 3,338,992 A | 8/1967 | Kinney | |
| 3,341,394 A | 9/1967 | Kinney | |
| 3,348,541 A | 10/1967 | Loebeck | |
| 3,368,668 A | 2/1968 | Micciche | |
| 3,448,478 A | 6/1969 | Nash et al. | |
| 3,485,706 A | 12/1969 | Evans | |

(Continued)

FOREIGN PATENT DOCUMENTS

DE    19620487    11/1997

(Continued)

OTHER PUBLICATIONS

PCT Search Report—Oct. 23, 2006.

(Continued)

*Primary Examiner*—David J Walczak
(74) *Attorney, Agent, or Firm*—Dority & Manning, P.A.

(57) ABSTRACT

A wipe includes a substrate with a pouch configured on an application side thereof. An access opening is provided into an internal space of the pouch. A composition delivered by the wipe upon use of the product is stored in a container that is inserted into the pouch through the access opening. Upon use of the wipe, the container within the pouch releases the composition, which is delivered through the pouch for application by the wipe.

29 Claims, 4 Drawing Sheets

U.S. PATENT DOCUMENTS

| | | | |
|---|---|---|---|
| 3,502,763 A | 3/1970 | Hartman | |
| 3,542,615 A | 11/1970 | Dobo et al. | |
| 3,589,823 A | 6/1971 | Hendrickson | |
| 3,675,264 A | 7/1972 | Storandt | |
| 3,692,618 A | 9/1972 | Dorschner | |
| 3,696,821 A | 10/1972 | Adams, IV | |
| 3,802,817 A | 4/1974 | Matsuki et al. | |
| 3,826,259 A | 7/1974 | Bailey | |
| 3,849,241 A | 11/1974 | Butin et al. | |
| 3,853,412 A | 12/1974 | Griffin | |
| 3,855,046 A | 12/1974 | Hansen et al. | |
| 3,902,509 A | 9/1975 | Tundermann et al. | |
| 3,905,113 A | 9/1975 | Jacob | |
| 3,952,867 A | 4/1976 | McCord | |
| 3,982,298 A | 9/1976 | Ota | |
| 4,041,203 A | 8/1977 | Brock et al. | |
| 4,084,586 A | 4/1978 | Hettick | |
| 4,100,324 A | 7/1978 | Anderson et al. | |
| 4,121,312 A | 10/1978 | Penney | |
| 4,154,542 A * | 5/1979 | Rasmason | 401/7 |
| 4,269,181 A | 5/1981 | Delannoy | |
| 4,323,534 A | 4/1982 | DesMarais | |
| 4,333,979 A | 6/1982 | Sciaraffa et al. | |
| 4,335,731 A | 6/1982 | Bora, Jr. | |
| 4,340,563 A | 7/1982 | Appel | |
| 4,414,970 A | 11/1983 | Berry | |
| 4,616,374 A | 10/1986 | Novogrodsky | |
| 4,617,694 A | 10/1986 | Bori | |
| 4,643,725 A | 2/1987 | Schlesser et al. | |
| 4,643,791 A | 2/1987 | Jurrius et al. | |
| 4,655,760 A | 4/1987 | Morman et al. | |
| 4,657,802 A | 4/1987 | Morman et al. | |
| 4,660,228 A | 4/1987 | Ogawa et al. | |
| 4,663,220 A | 5/1987 | Wisneski et al. | |
| 4,665,901 A | 5/1987 | Spector | |
| 4,707,398 A | 11/1987 | Boggs | |
| 4,720,415 A | 1/1988 | Vander Wielen et al. | |
| 4,724,184 A | 2/1988 | Killian et al. | |
| 4,733,410 A | 3/1988 | Glotkin | |
| 4,741,949 A | 5/1988 | Morman et al. | |
| 4,766,029 A | 8/1988 | Brock et al. | |
| 4,781,966 A | 11/1988 | Taylor | |
| 4,789,699 A | 12/1988 | Kieffer et al. | |
| 4,803,117 A | 2/1989 | Daponte | |
| 4,818,464 A | 4/1989 | Lau | |
| 4,820,572 A | 4/1989 | Killian et al. | |
| 4,825,470 A | 5/1989 | Horio | |
| 4,828,556 A | 5/1989 | Braun et al. | |
| 4,834,738 A | 5/1989 | Kielpikowski et al. | |
| 4,858,245 A | 8/1989 | Sullivan et al. | |
| 4,875,247 A | 10/1989 | Berg | |
| 4,884,581 A | 12/1989 | Rescigno | |
| 4,920,974 A | 5/1990 | Roth et al. | |
| 4,923,742 A | 5/1990 | Killian et al. | |
| 4,926,851 A | 5/1990 | Bulley | |
| 4,965,122 A | 10/1990 | Morman | |
| D313,317 S | 1/1991 | Brunner et al. | |
| 4,981,747 A | 1/1991 | Morman | |
| 4,998,978 A | 3/1991 | Varum | |
| 5,036,551 A | 8/1991 | Dailey et al. | |
| 5,057,368 A | 10/1991 | Largman et al. | |
| 5,068,941 A | 12/1991 | Dunn | |
| 5,093,422 A | 3/1992 | Himes | |
| 5,108,820 A | 4/1992 | Kaneko et al. | |
| 5,108,827 A | 4/1992 | Gessner | |
| 5,114,781 A | 5/1992 | Morman | |
| 5,116,662 A | 5/1992 | Morman | |
| 5,120,758 A | 6/1992 | Satoh | |
| 5,123,113 A | 6/1992 | Smith | |
| 5,133,971 A | 7/1992 | Copelan et al. | |
| 5,169,706 A | 12/1992 | Collier, IV et al. | |
| 5,181,914 A | 1/1993 | Zook | |
| 5,213,428 A | 5/1993 | Salman | |
| 5,226,992 A | 7/1993 | Morman | |
| 5,228,433 A | 7/1993 | Rosen | |
| 5,277,976 A | 1/1994 | Hogle et al. | |
| 5,280,661 A | 1/1994 | Brown | |
| 5,283,924 A | 2/1994 | Kaminski et al. | |
| 5,287,584 A | 2/1994 | Skinner | |
| 5,294,482 A | 3/1994 | Gessner | |
| 5,304,599 A | 4/1994 | Himes | |
| 5,320,531 A | 6/1994 | Delizo-Madamba | |
| 5,332,613 A | 7/1994 | Taylor et al. | |
| 5,336,545 A | 8/1994 | Morman | |
| 5,336,552 A | 8/1994 | Strack et al. | |
| 5,348,153 A | 9/1994 | Cole | |
| 5,356,005 A | 10/1994 | Burrello | |
| 5,362,306 A | 11/1994 | McCarver et al. | |
| 5,382,400 A | 1/1995 | Pike et al. | |
| 5,383,846 A | 1/1995 | Short | |
| 5,389,202 A | 2/1995 | Everhart et al. | |
| 5,439,487 A | 8/1995 | Stanitzok | |
| 5,440,774 A | 8/1995 | Cole | |
| 5,445,825 A | 8/1995 | Copelan et al. | |
| 5,464,688 A | 11/1995 | Timmons et al. | |
| 5,466,410 A | 11/1995 | Hills | |
| 5,474,525 A | 12/1995 | Blott | |
| 5,486,381 A | 1/1996 | Cleveland et al. | |
| 5,487,201 A | 1/1996 | Hansen et al. | |
| 5,502,863 A | 4/1996 | Perkins | |
| 5,503,908 A | 4/1996 | Faass | |
| 5,507,641 A | 4/1996 | Cline | |
| 5,524,764 A | 6/1996 | Kaufman et al. | |
| 5,529,665 A | 6/1996 | Kaun | |
| 5,541,388 A | 7/1996 | Gadd | |
| 5,554,076 A | 9/1996 | Clark | |
| 5,591,510 A | 1/1997 | Junker et al. | |
| 5,636,405 A | 6/1997 | Stone et al. | |
| 5,678,273 A | 10/1997 | Porcelli | |
| 5,752,926 A | 5/1998 | Larson et al. | |
| 5,765,252 A | 6/1998 | Carr | |
| 5,766,248 A | 6/1998 | Donovan | |
| 5,770,229 A | 6/1998 | Tanihara et al. | |
| 5,771,522 A | 6/1998 | Carmody | |
| 5,794,774 A | 8/1998 | Porcelli | |
| 5,804,021 A | 9/1998 | Abuto et al. | |
| 5,819,765 A | 10/1998 | Mittiga | |
| 5,826,599 A | 10/1998 | Adams | |
| 5,834,002 A | 11/1998 | Athanikar | |
| 5,875,513 A | 3/1999 | Reinold | |
| 5,909,739 A | 6/1999 | Masrour-Rad | |
| 5,911,319 A | 6/1999 | Porcelli et al. | |
| 5,953,783 A | 9/1999 | Hahn | |
| 6,019,773 A | 2/2000 | Denmark | |
| 6,065,480 A | 5/2000 | Mader | |
| 6,105,587 A | 8/2000 | Dunn | |
| 6,112,356 A | 9/2000 | Hashey | |
| 6,139,514 A | 10/2000 | Benson | |
| 6,206,596 B1 * | 3/2001 | Johnson | 401/6 |
| 6,336,461 B1 | 1/2002 | Martinez | |
| 6,409,059 B1 | 6/2002 | Calvert | |
| 6,420,624 B1 | 7/2002 | Kawase | |
| 6,420,625 B1 | 7/2002 | Jones et al. | |
| 6,494,767 B2 | 12/2002 | Fisher | |
| 6,508,602 B1 | 1/2003 | Gruenbacher et al. | |
| 6,647,549 B2 | 11/2003 | McDevitt et al. | |
| 6,721,987 B2 | 4/2004 | McDevitt et al. | |
| 6,898,819 B2 | 5/2005 | Tanaka et al. | |
| 2002/0102392 A1 | 8/2002 | Fish et al. | |
| 2003/0050589 A1 | 3/2003 | McDevitt et al. | |

FOREIGN PATENT DOCUMENTS

| | | |
|---|---|---|
| EP | 0303528 | 7/1988 |

| | | |
|---|---|---|
| EP | 0638277 A1 | 2/1995 |
| EP | 0985364 A2 | 3/2000 |
| EP | 0985364 A3 | 3/2000 |
| EP | 0985364 B1 | 3/2000 |
| EP | 1 495 704 A1 | 1/2005 |
| FR | 2848535 | 6/2004 |
| GB | 2099305 A | 12/1982 |
| GB | 2227938 A | 8/1990 |
| GB | 1046146 | 10/1996 |
| WO | WO 8707122 | 12/1987 |
| WO | WO 9203947 | 3/1992 |
| WO | WO 9531154 | 11/1995 |
| WO | WO 9955271 | 11/1999 |

OTHER PUBLICATIONS

Medical Textiles, Nov. 1999 "Crimped Bristle Toothbrush". "Nonwoven Removes Stains", "Dental Floss".

Tetra Medical Supply Corp.; Product Information; Jan. 4, 2000; www.tetramed.com/dress.htm.

Spandage; Product Information; Jan. 4, 2000; spandage.com/main.htm.

FootSmark Products; Product Information—Toe Caps & DigiCushions; Jan. 4, 2000; www.footsmart.com.

Abstract of Japanese Patent No. JP06205723.

Abstract of Japanese Patent No. JP06285108.

Abstract of Japanese Patent No. JP10243818.

Abstract of Japanese Patent No. JP05044165.

* cited by examiner

DISPOSABLE WIPE WITH LIQUID STORAGE AND APPLICATION SYSTEM

BACKGROUND OF THE INVENTION

Disposable finger covers or wipes are known and used in the art for a variety of purposes. A common use of finger wipes (also know as "finger gloves" in the art) is for applying ointments, medications, alcohol, oral anesthetics, and the like, to various body parts. Such devices may also be utilized to remove various substances, such as makeup, or to clean body parts or other objects.

Finger wipes have proven particularly useful in the field of dental hygiene in that they provide a portable and efficient means for more frequent dental care, and as a cleaning device that can be easily used in public. In particular, a number of finger-mounted teeth cleaning devices have been developed that can be placed over a finger and wiped over the teeth and gums. These devices are typically small, portable, and disposable.

Examples of dental hygiene cleaning devices and finger wipes are disclosed, for instance, in U.S. Pat. No. 6,721,987 to McDevitt, et al. and in U.S. Pat. No. 6,647,549 also to McDevitt, et al., which are incorporated herein by reference. A dental hygiene finger device is also described in U.S. Pat. No. 5,445,825 to Copelan et al. Other finger-mounted teeth cleaning devices were developed to contain an elastomeric material to help prevent the device from slipping or falling off the user's finger during cleaning. Examples of such teeth cleaning devices are disclosed in U.S. Pat. No. 5,068,941 to Dunn; U.S. Pat. No. 5,348,153 to Cole; U.S. Pat. No. 5,524,764 to Kaufman et al.; and PCT Publication No. WO 95/31154 to Mittiga et al.

Finger wipes that incorporate an integral additive or composition are a convenient and desirable product. However, it may be difficult to incorporate an adequate supply of the desired composition with conventional finger wipe constructions. Consumers often resort to using multiple wipes to achieve a desired application of the composition.

DEFINITIONS

As used herein, the terms "elastic" and "elastomeric" are generally used to refer to materials that, upon application of a force, are stretchable to a stretched, biased length, and which will retract at least about 50% of its elongation upon release of the stretching, biasing force.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Meltblown fibers may be continuous or discontinuous, are generally smaller than 10 microns in average diameter, and are generally tacky when deposited on a collecting surface.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992; 4,981,747; 4,965,122; and 5,336,545, all to Morman, all of which are incorporated herein by reference thereto.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel, et al.; U.S. Pat. No. 3,692,618 to Dorschner, et al.; U.S. Pat. No. 3,802,817 to Matsuki, et al.; U.S. Pat. No. 3,338,992 to Kinney; U.S. Pat. No. 3,341,394 to Kinney; U.S. Pat. No. 3,502,763 to Hartman; and U.S. Pat. No. 3,542,615 to Dobo, et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen, et al., which is incorporated herein by reference. Other composite elastic materials are described and disclosed in U.S. Pat. No. 4,789,699 to Kieffer, et al.: U.S. Pat. No. 4,781,966 to Taylor: U.S. Pat. No. 4,657,802 to Morman; and U.S. Pat. No. 4,655,760 to Morman, et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like.

SUMMARY

Objects and advantages of the invention will be set forth below in the following description, or may be obvious from the description, or may be learned through practice of the invention.

The present disclosure is directed generally to an article used to deliver a composition from a container configured with the article. The article may be a generally flat member, such as a disposable towel or the like, or may be in the form of a tubular structure designed to fit over a user's hand or one or more fingers. The article is collectively referred to herein as a "wipe", and for ease of description only, aspects of the invention are explained by reference to finger wipe embodiments that fit over one or more fingers. However, it should be appreciated that the invention is not limited to such finger wipes, and includes all embodiments of wipes incorporating the novel aspects of the invention.

A wipe of the present invention can also be used in various applications. For instance, the wipe may be used to clean or treat parts of the body such as the eyes, the ears, the nose, and the like. The wipe may be used to apply a medicine, lotion, ointment, cleaning agent, or the like to any part of the body, or any other object. In still other embodiments, the wipe can be used to clean various utensils, objects or surfaces and/or to polish various items with any number of compositions or agents carried by the wipe. For example, in one embodiment, the wipe can be used to polish silver with a polish carried by the wipe.

In a particular embodiment, the wipe includes a substrate having an application side and an opposite back side. The substrate may be formed as a tubular structure having an open end for the insertion of one or more fingers, or may be a component of such a tubular structure. A pouch is configured on the application side of the substrate and includes an access opening into the pouch. The opening can be located anywhere on the pouch. In a particular embodiment, the opening is oriented towards the closed end of the tubular structure, or towards the open end of the tubular structure.

Any manner of desired composition or additive intended to be delivered by the wipe upon use of the product is stored in a container that is insertable into the pouch through the access opening. In use of the wipe, the container releases the composition within the pouch and the composition migrates through the pouch material for application by the wipe. The pouch material may be a liquid permeable material, or an impermeable material that has been altered, for example with slits or holes, so as to be permeable to the composition The composition container may be any one of a number of suitable devices. In a particular embodiment, the container is formed of a shell designed to rupture upon application of pressure to the pouch. For example, the container may be a gel capsule that ruptures to release the composition held therein. In an alternate embodiment, the container may be a relatively hard-sided vial or like device that is crushed upon application of pressure, with the vial components being retained within the pouch during use of the wipe. With still another embodiment, the container may be formed by a shell or membrane that dissolves upon exposure to a liquid during use of the finger wipe such that the composition is released and mixes with the liquid.

It should be appreciated that the invention is not limited to any particular type of composition or intended use of the wipe. The composition may be a liquid or cream agent. In an alternate embodiment, the composition may be in a powder or granular form that mixes with a liquid upon use of the finger wipe.

The components of the wipe may be made of various suitable materials. In a particular embodiment, the substrate may be formed from a laminate of a liquid impermeable material and an outer nonwoven cover material. The pouch may be formed by a liquid permeable nonwoven patch of material that is attached to the cover layer. In this manner, the laminate material defines a back surface of the pouch and the access opening is defined between the laminate material and the patch. In a finger wipe embodiment, the liquid impermeable layer of the laminate prevents the composition from migrating through the tubular structure to the wearer's finger.

In an alternate embodiment, the pouch may be a separately formed member having a liquid impermeable backing layer that is attached to the application side of the substrate.

The pouch may be formed of an elastomeric material that stretches to accommodate the composition container, and then contracts to maintain the container within the pouch.

It may be desired to incorporate a seal with the pouch opening so as to minimize migration of the composition out of the access opening upon application of pressure to the pouch. In a particular embodiment, the seal may include a releasable adhesive applied between the pouch material and substrate along the access opening. A peel strip may be used to protect the adhesive prior to use of the wipe. In an alternate embodiment, the seal may be a hook-and-loop type of mechanism. For example, the substrate may include a nonwoven material, and the pouch may include a strip of microhook material along the access opening that releasably secures to the nonwoven material.

The pouch may be configured to retain a single composition container, or a plurality of containers. The containers may be stored within the pouch prior to use of the wipe, or may be stored separately from the wipe. For example, a plurality of the wipes and a selection of composition containers may be provided in a kit format wherein the consumer chooses an appropriate composition depending on the intended use of the wipe.

Because the composition is applied through the pouch material, it may be desired that the pouch material include a texturized outwardly facing surface, particularly if the wipe is intended as a cleaning or dental hygiene device. In this regard, the pouch may be formed from a nonwoven material layer that has been texturized by any one of a number of conventional processes.

The tubular structure component of finger wipe embodiments can be made from numerous different types of materials. For instance, in one embodiment, nonwoven webs made from synthetic and/or pulp fibers may be used. The material may include a texturized surface adapted to enhance scrubbing or cleaning with the finger wipe. Further, a material can also include an elastic component for providing the tubular structure with form-fitting properties. A moisture barrier, such as a liquid impermeable layer, may be incorporated into the finger wipe to prevent any fluids from contacting the wearer's fingers. In general, a moisture barrier refers to any barrier, layer, or film that is relatively liquid impervious. The moisture barrier prevents the flow of liquid through the finger wipe so that a user's finger remains dry when the wipe is being used. In some embodiments, the moisture barrier can remain breathable, i.e., permeable to vapors, such that a finger within the wipe is more comfortable. Examples of suitable moisture barriers can include films, fibrous materials, laminates, and the like. The wipe may include an elastic nonwoven material having form-fitting properties to help the wipe effectively remain on a finger in use. Suitable materials will be described in greater detail below.

A finger wipe of the present invention can generally be formed in a variety of ways. For instance, the tubular structure can be formed from two or more sections of the same or a different substrates, depending on the desired characteristics of the finger wipe. For example, in one embodiment, the tubular structure is formed from two substrate sections, wherein one section may be formed from a textured nonwoven material and the other section may be formed from an elastomeric nonwoven material. A seam is formed around the closed periphery portion of the wipe to define the elongated closed-end tubular structure having the finger insertion opening at one end. The pouch may be formed with the tubular structure during the seaming process. For example, the pouch may be defined by a patch of material that is sealed along a portion of the periphery of the tubular structure.

Besides the composition contained within the pouch, various other additives can also be applied to other portions of the cover layer during manufacturing and/or by the consumer. For example, cationic materials, such as chitosan (poly-N-acetylglucosamine), chitosan salts, cationic starches, etc., can be applied to a wipe of the present invention to help attract negatively charged bacteria and deleterious acidic byproducts that accumulate in plaque. Examples of other suitable additives include, but are not limited to, dental agents, such as fluorides, peppermint oil, mint oil and alcohol mixtures; flavoring agents, such as xylitol; anti-microbial agents; polishing agents; hemostatic agents; surfactants; anti-ulcer components; and the like.

Additives can be applied to the substrate material in the form of an aqueous solution, non-aqueous solution (e.g., oil), lotions, creams, suspensions, gels, etc. When utilized, the aqueous solution may be coated, saturated, sprayed, or impregnated into the material. In some embodiments, the additives can be applied asymmetrically. Moreover, in some instances, it may be desired that the additives comprise less than about 100% by weight of the wipe, and in some embodiments, less than about 50% by weight of the wipe, and particularly less than 10% by weight of the wipe.

The invention also encompasses any manner of kit or other compilation that includes a plurality of the wipes and containers in a common package, wherein the containers are filled with the same or different compositions. For example, a package may be provided to consumers that contains a number of disposable finger wipe embodiments with a plurality of rupturable containers having the same or different oral hygiene compositions.

It should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91 to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
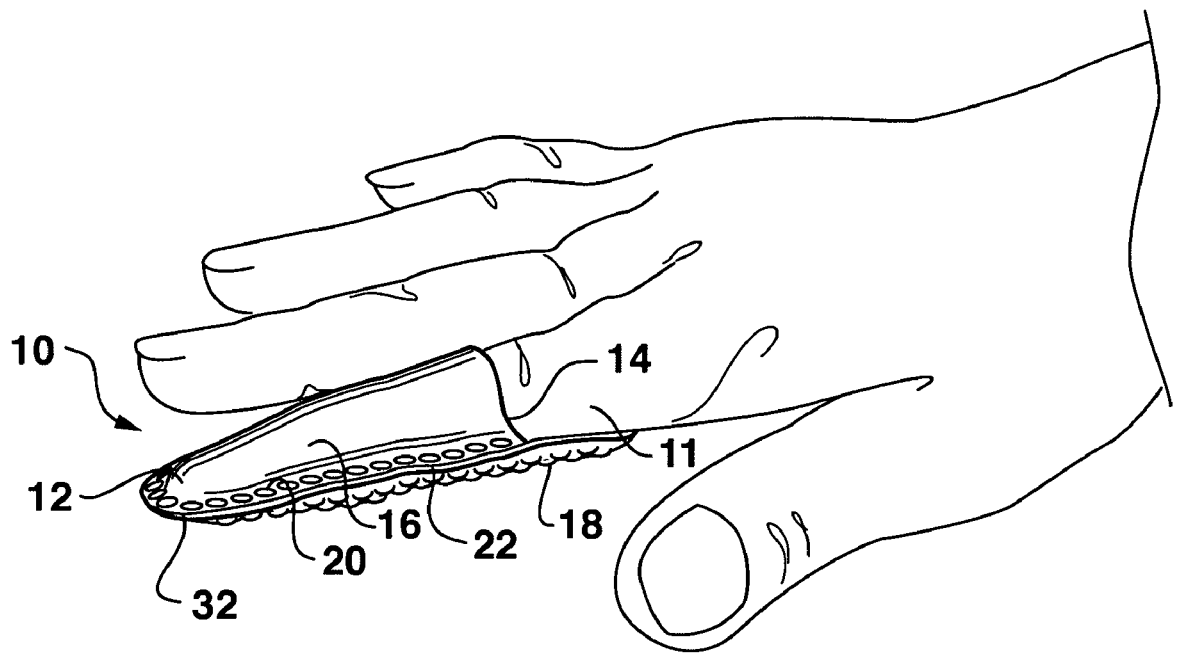
FIG. 1 is a perspective view of a finger wipe on a finger according to one embodiment of the present invention.

Repeat use of reference characters in the present specification and drawings is intended to represent the same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Embodiments of wipes 10 are illustrated in the figures as devices intended to be placed over one or more of a user's fingers 11 for use as a cleaning or polishing device, or any other use. In the illustrated embodiments, the finger wipe 10 is made from a first substrate section 16 and a second substrate section 18. The substrate sections may be panels or pieces of the same or a different material, and are bonded or attached together along an edge seam 22 in a finger-shaped pattern so that the bonded sections form a closed end tubular structure 12 with an opening 14 for the insertion of a finger. The substrate sections may be bonded or attached by any conventional means, including thermal or ultrasonic bonding of point bonds 20 around the seam 22. The sections 16 and 18 may be bonded or otherwise attached along the seam 22 in continuous strips of respective materials, with the sections 16 and 18 then being cut adjacent to the seams such that the finger-shaped wipe 10 is formed. In an alternative embodiment, the sections 16 and 18 are cut and bonded in a single processing step.

It should be appreciated that a wipe 10 according to the invention also includes single substrate components (i.e., a single substrate section 18), such as towels, disposable wipes, and the like, that incorporate the novel pouch configuration on an application side thereof, as described in greater detail below.

It may be desired that one or both of the sections 16, 18 include a textured outer surface, such as the surface 30 of the second section 18, to enhance the cleaning or scrubbing effect of the wipe. A well known method for forming a textured surface in a nonwoven material is a thermal bonding process wherein raised unbonded (or lightly bonded) areas are surrounded by bonded regions, sometimes referred to in the art as a "point unbonded (PUB) material. A textured material formed by such a process may be desired as an outer cover layer 28 in finger wipes 10 according to the invention, in that it provides raised "bumps" on the surface 30, as illustrated in the figures.

Figure 2:
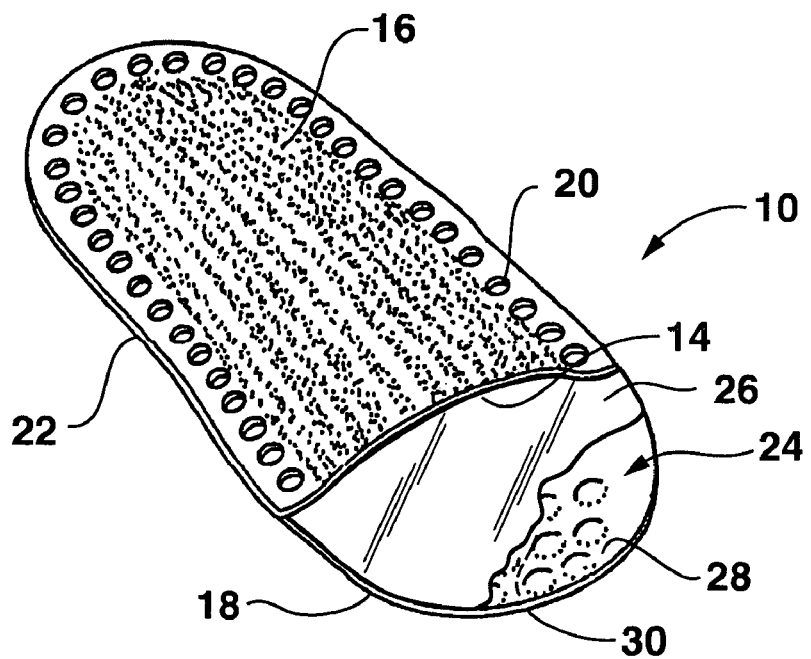
FIG. 2 is a perspective view of an upper side of the finger wipe shown in FIG. 1.

Referring to FIG. 2, the second substrate section 18 may have a length greater than the first substrate section 16 such that the second section 18 includes a longitudinally extending portion 24 that extends beyond the edge of the first section 16. This portion 24 may serve as a "pull-on" tab and can facilitate placement of the finger wipe 10 over the user's finger.

Figure 5A:
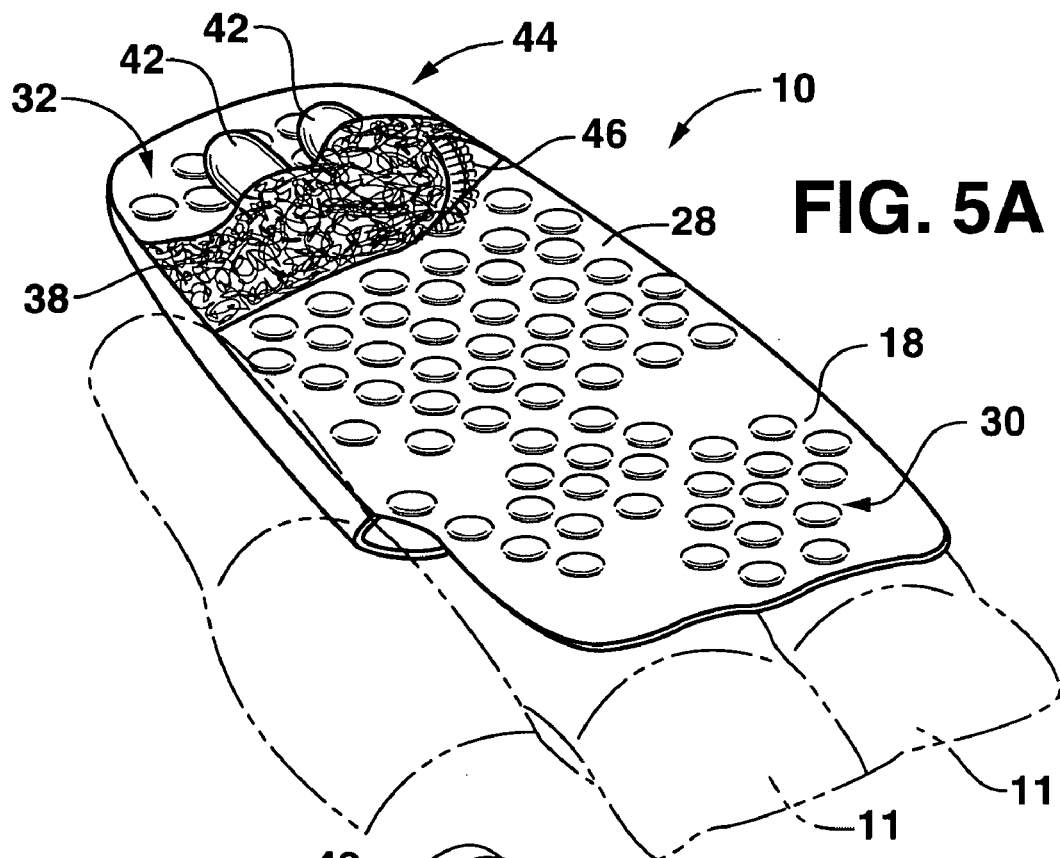
FIG. 5A is a lower side view of an embodiment of a two-finger wipe incorporating a seal with the pouch.
Figure 5B:
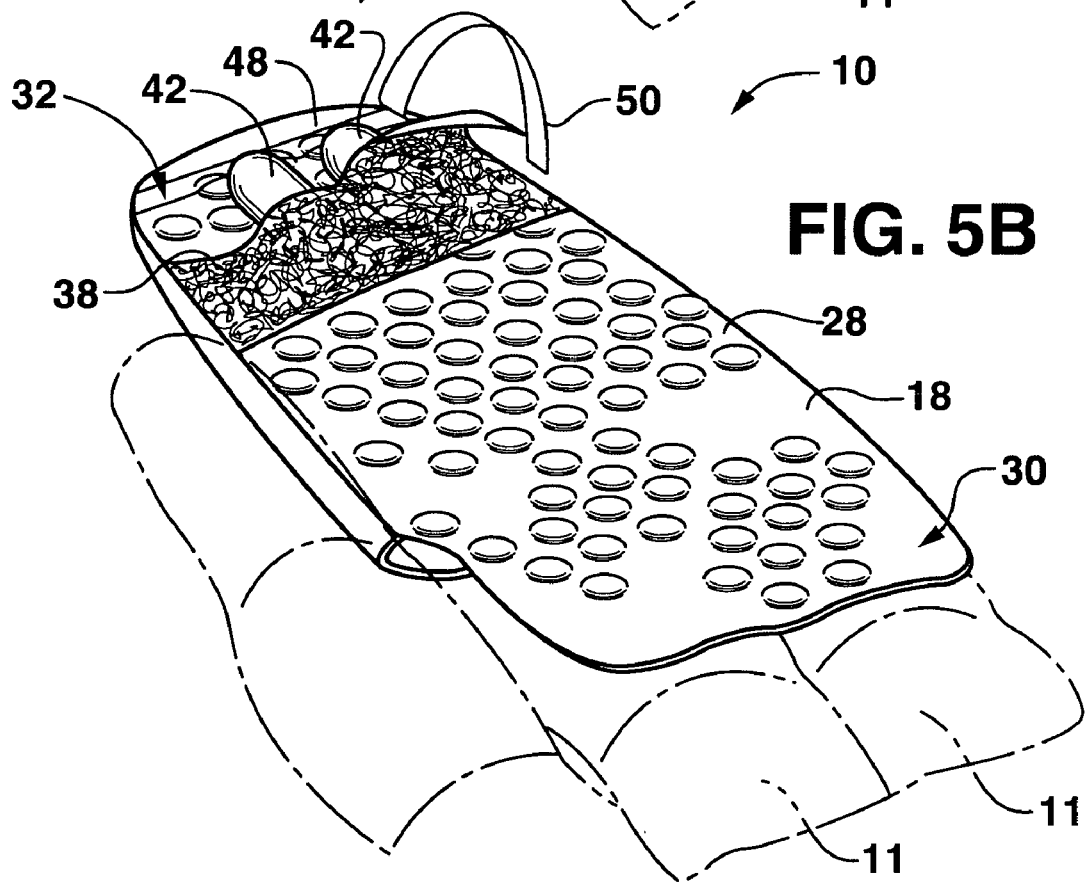
FIG. 5B is a lower side view of another two-finger wipe incorporating a different type of seal with the pouch and an access opening into the pouch oriented towards the closed end of the tubular structure.

The dimensions of the wipes 10 will depend upon the particular application and purpose for which the wipe is to be used. For instance, in a finger wipe embodiment, the tubular structure is constructed to fit around the finger of an adult or the finger of a child. Further, the finger wipe can also be constructed to fit around two or more fingers, as seen in FIGS. 5A and 5B. For most single finger wipes, the wipe should have a length of from about 1 inch to about 7 inches and a median flattened width of from about 0.5 inches to about 4 inches. When constructed to fit around two fingers, the finger wipe can have a median width of from about 0.75 inches to about 2.5 inches, depending on the elasticity of the wipe.

In general, the finger wipes 10 of the present invention can be formed from a variety of materials. U.S. Pat. No. 6,647,549 incorporated herein by reference describes various suitable materials, and combinations of materials, that may be used for wipes 10. Non-limiting examples of suitable materials are also described in greater detail below.

Referring to the figures in general, the wipes 10 include a pouch 32 configured on the application side (outwardly facing) of the substrate 18 generally at the closed end of the tubular structure 12. The pouch 32 includes an access opening 33 into the internal volume or space of the pouch 32. The opening 33 may be located anywhere along the periphery of the pouch, or in the pouch 32. For example, in the embodiments of FIGS. 3, 4, and 5A, the opening 33 is at the side of the pouch closest to the open end of the tubular structure 12. In the embodiment of FIG. 5B, the opening is at the side of the pouch closest to the closed end of the tubular structure 12.

Figures 3, 4:
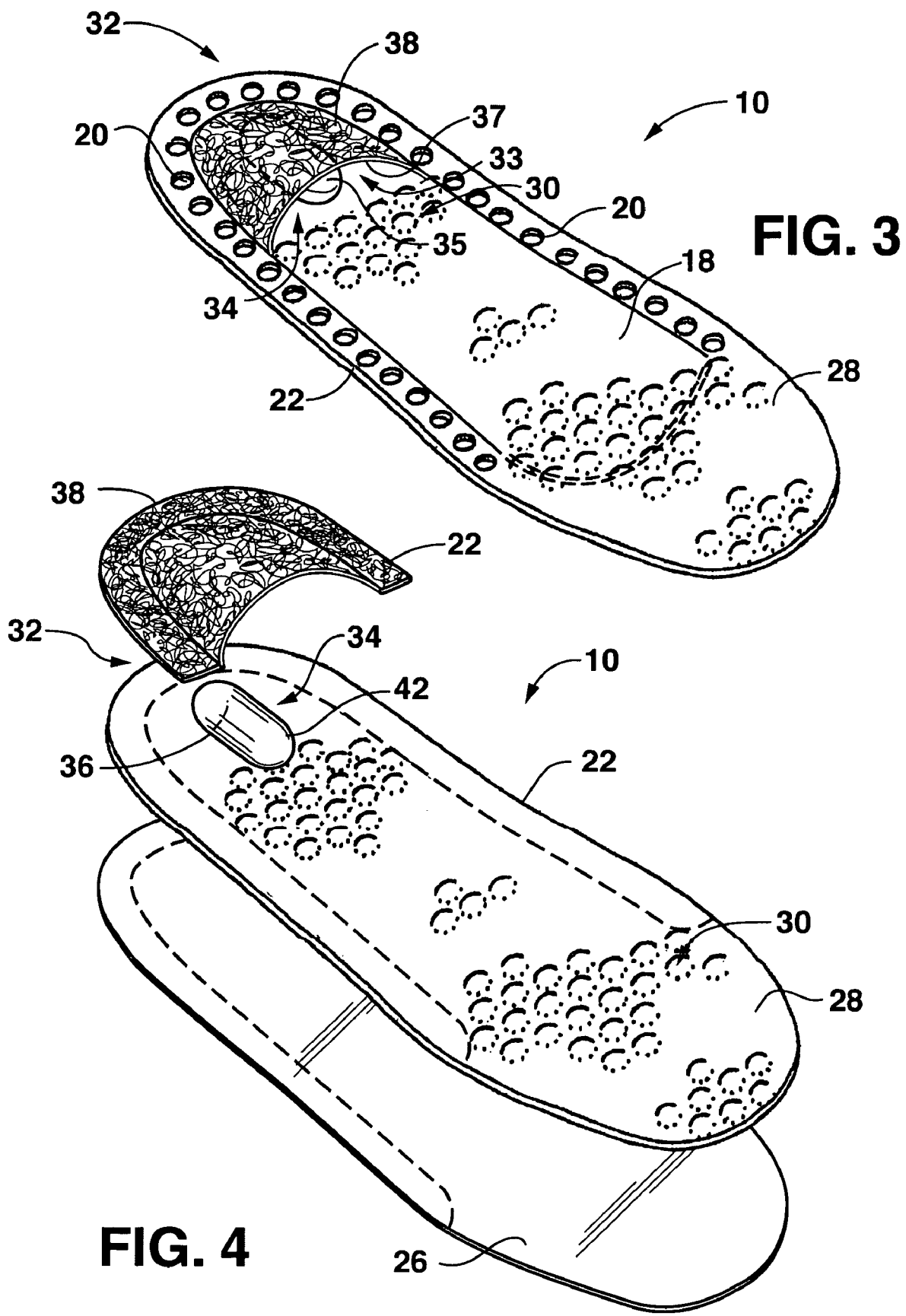
FIG. 3 is a perspective view of a lower side of the finger wipe shown in FIG. 1 particularly illustrating an embodiment of a pouch configuration.
FIG. 4 is an exploded component view of the lower side of the finger wipe shown in FIG. 3.

The outer wall of the pouch 32 is formed by a material 38 that may be liquid permeable, such as a suitable nonwoven material, or liquid impermeable with holes, apertures, or the like defined therein. The pouch 32 includes a back wall that may be defined by a cover layer 28 of the second section 18, as illustrated in FIGS. 3 and 4. The material 38 defining the front wall of the pouch 32 may be attached to the substrate 18 by any conventional means, including bonding, adhesives, welding, and so forth. In a particular embodiment, the material 38 is bonded with substrates 18 and 16 in a single bonding process wherein the material 38, and first and second substrates 16, 18 are all bonded along the peripheral seam 22 in a single bonding process.

In an alternate embodiment, the outer pouch wall material 38 may be a portion of the substrate 18 that has been folded back over the substrate and bonded along the side seams.

The pouch 32 is configured to securely hold a container 34 of any desired composition 36 intended to be delivered by the finger wipe 10 upon use of the wipe wherein the container 34 releases the composition 36, which then migrates through the pouch material 38.

The composition container 34 may be any one of a number of suitable devices. In a particular embodiment, the container is formed of a wall or shell 35 that is designed to rupture upon application of pressure to the pouch 32, for example by the user pressing the wipe 10 against a surface. In a particular embodiment, the container 34 is a gel capsule 42 that ruptures to release the composition held therein. Such gel capsules are well known and widely used for various purposes. Examples include gel capsules for delivering medications, vitamins, and the like. Gel capsule technology is often referred to as macroencapsulation, which is also the technology used to manufacture paint balls.

It should be appreciated that the invention is not limited to the type, size, or number of capsules 42, or other suitable containers 34, inserted into the pouch 32.

In an alternate embodiment, the container 34 may be a relatively hard-sided vial or like device that is crushed upon application of pressure to the pouch 32, with the vial components being retained within the pouch during use of the wipe 10.

In still another embodiment, the container 34 may be formed by a shell or membrane that dissolves upon exposure to a liquid during use of the finger wipe 10. Dissolvable capsules are conventionally used with many types of over-the-counter (OTC) medications, and are well known to those skilled in the art.

It should be appreciated that the invention is not limited to any particular type of composition 36 released from the container 34. The composition may be any type of liquid or cream agent or additive. In an alternative embodiment, the composition may be in a powder form that mixes with a liquid upon release from the container 34. Various non-limiting examples of compositions 36 that may be used with wipes 10 according to the invention are described in greater detail below.

The tubular structure component 12 may be made of various suitable materials, a number of which are discussed below. In a particular embodiment, the substrate 18 of the tubular structure 12, which is the side incorporating the pouch 32, is formed from a laminate material of a liquid impermeable layer 26 and a nonwoven cover layer 28, as particularly illustrated in FIGS. 4 and 6. The pouch outer material 38 may be formed from the same type of nonwoven material as the cover layer 28. In this embodiment, the laminate material defines the back wall or surface of the pouch 32, and the liquid impermeable layer 26 prevents the composition 36 from migrating through the tubular structure 12 to the wearer's finger. Thus, in this particular embodiment, the opening 33 into the pouch 32 is defined between the pouch outer material 38 and the cover layer 28 of the substrate 18.

Figure 6:
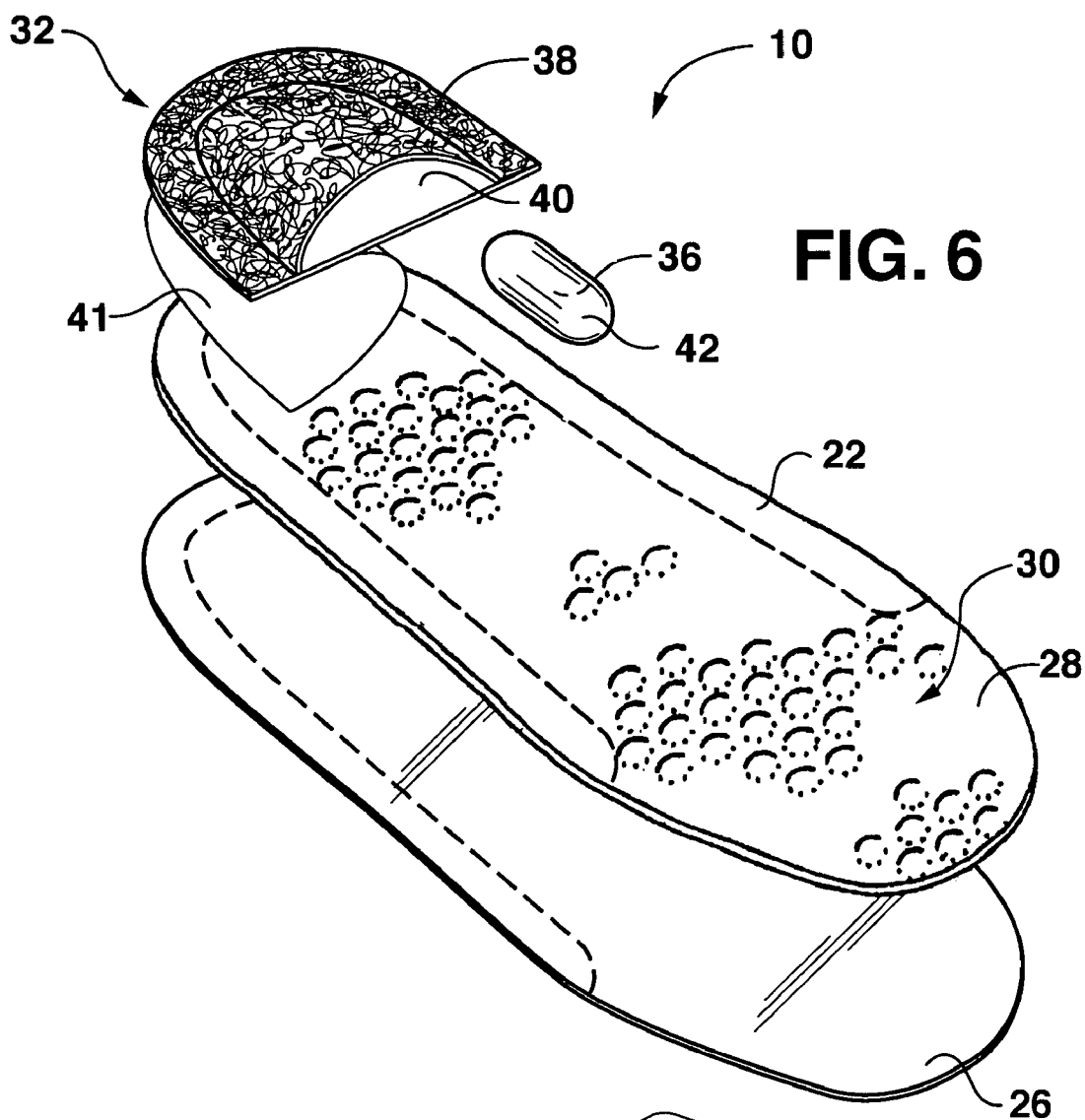
FIG. 6 is an exploded component view of the lower side of an alternate embodiment of wipe wherein the pouch incorporates a backing layer attached to the wipe surface.

In an alternate embodiment illustrated in FIG. 6, the pouch 32 includes a dedicated or separate backing layer 40 formed of a liquid impermeable material. The backing layer 40 may be attached to the substrate 18 by any suitable means, including an adhesive layer or strip 41. With this particular embodiment, the pouch 32 may be formed separate from the substrate 18 and later applied to the substrate.

The composition containers 34 should be securely held within the pouch 32 prior to and during use of the finger wipes 10. In a particular embodiment, the pouch cover material 38 may be formed at least in part from an elastic material that stretches to accommodate the composition containers 34, and then contracts to maintain the containers within the pouch 32. Various types of suitable elastic or elastomeric materials are discussed below.

In an alternative embodiment, a sealing mechanism 44 may be provided to seal the edges of the pouch 32 to the cover layer 28 of the section 18. For example, in FIG. 5A, the seal mechanism 44 includes a strip of hook material 46 attached along the open edge of the pouch 32. This strip of microhook material may attach directly to the outer cover layer 28, particularly if the outer cover layer is a nonwoven material. With this configuration, the open edge of the pouch 32 is releasably sealed to the cover layer 28. In an alternative embodiment illustrated in FIG. 5B, an adhesive strip 48 is disposed between the open edge of the seal 32 and the cover layer 28. A peel strip 50 may be removed from the adhesive strip 48 prior to pressing the open edge of the pouch 32 to the adhesive strip 48. It should be appreciated that the adhesive strip 48 may be applied to the underside of the pouch material 38, or to the upper side of the second section 18 of the finger wipe 10, for example as a strip across the cover layer 28.

Because the composition 36 is applied through the pouch material 38, it may be desired that the material 38 also include a texturized outwardly facing surface, particularly if the wipe 10 is intended as a cleaning or scrubbing device. In this regard, the pouch material 38 may be formed from a nonwoven material layer that has been texturized by any one or number of conventional processes, as discussed with respect to the outer cover layer 28 of the second section 18.

The tubular structure 12 may include an elastic component or material for providing the structure with form-fitting properties. Examples of suitable elastomeric materials are discussed below.

It should be appreciated that, in addition to the composition 36 contained within the containers 34, various other additives can be applied to other surfaces of the finger wipes 10 during manufacture of the wipes, or by the consumer. For example, additives can be applied to the tubular structure material in the form of an aqueous solution, non-aqueous solution, lotion, cream, suspensions, gels, etc. Examples of suitable additives include dental agents such as fluorides, peppermint oil, mint oil, and alcohol mixtures; flavoring agents; anti-microbial agents; polishing agents; hemostatic agents, surfactants, anti-ulcer components, and so forth.

Figure 7:
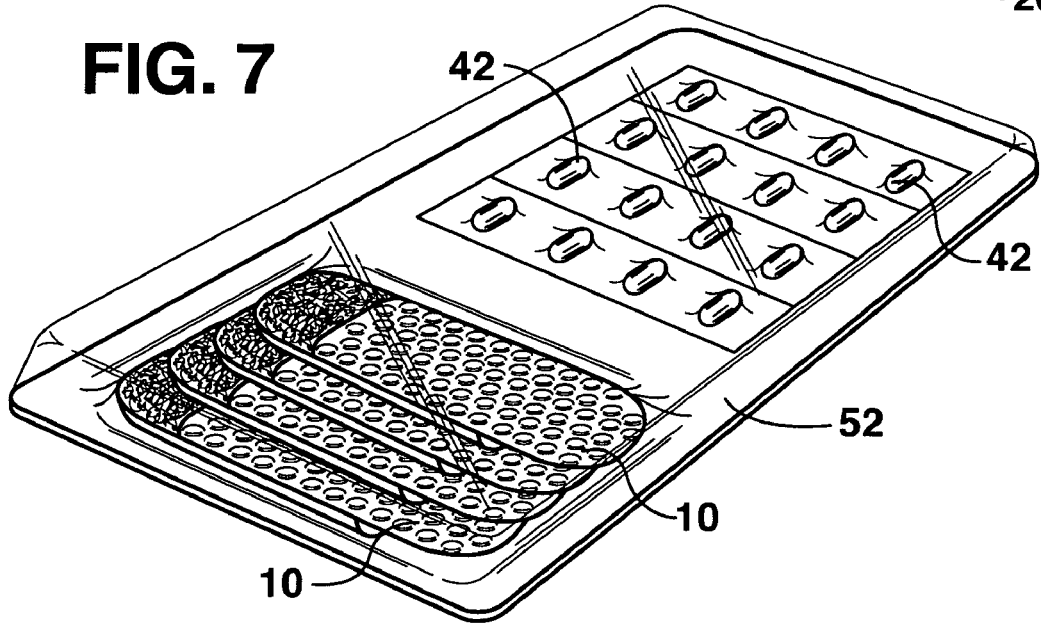
FIG. 7 is a perspective view of a package of wipes and composition containers.

The wipes 10 and composition containers 34 may be supplied to the consumers in any number of configurations. For example, the products may be prepackaged such that the gel capsules 42 are pre-inserted into the pouches 32. In an alternative embodiment, the composition containers 34 may be supplied separate from the wipes 10. For example, referring to FIG. 7, a package 52 is illustrated wherein a number of gel capsules 42 are supplied with a number of wipes 10. The capsules 42 may comprise a variety of different compositions, or the same composition. The consumer may use any one or combination of the gel capsules 42 with any combination of the wipes 10. It should be appreciated that any number of packaging configurations are contemplated for providing the consumer with various combinations of composition containers 42 and finger wipes 10.

Referring to FIGS. 1, 5A, and 5B, the capsules 42 may be ruptured by application of pressure. For example, the capsules 42 may be positioned within the pouch 32 so as to be pressed by the user's fingers against a surface until the capsules rupture. In an alternate embodiment, the capsules 42 may be disposed within the pouch 32 so as to be positioned between a user's fingers. The capsules are then ruptured by the user squeezing the capsules between their fingers. Any structure may be provided within the pouch 32 to retain the capsules 42 at any desired location.

Various non-limiting examples of materials that may be used in construction of finger wipes 10 according to the invention are discussed below.

Base Web Materials

As mentioned, the first section 16 and the second section 18 of the tubular component 12, as well as the pouch material 38, are formed from a base web that may include one or more layers of fibrous materials used in the art for making wipes. For example, either or both of the sections may comprise a liquid absorbent material or a non-absorbent material. When comprising a liquid absorbent material, the base webs may comprise any suitable fabric material, such as a woven fabric, a nonwoven fabric, or a knitted fabric.

In one embodiment, the base web comprises a spunbond web, a coform web, a tissue web, a meltblown web, a bonded carded web, and laminates thereof. A nonwoven material can be made from various fibers, such as synthetic or natural fibers. For instance, in one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Many polyolefins are available for fiber production, for example polyethylenes such as Dow Chemical's PE XU 61800.41 linear low-density polyethylene ("LLDPE") and 25355 and 12350 high-density polyethylene ("HDPE") are such suitable polymers. Fiber-forming polypropylenes include Exxon Chemical Company's Escorene PD 3445 polypropylene and Montell Chemical Co.'s PF-304 and PF-015. Many other polyolefins are commercially available and include polybutylenes and others.

Synthetic fibers added to the nonwoven web can also include staple fibers that can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides, or in addition to, synthetic fibers, pulp fibers can also be used in the materials. The pulp fibers used in forming the cover layer may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the base web can include a hydraulically entangled web (or hydroentangled). Hydroentangled webs, which are also known as spunlace webs, refer to webs that have been subjected to columnar jets of a fluid that cause the fibers in the web to entangle. For example, in one embodiment, the cover layer can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wis. Hydraulic entangling may be accomplished utilizing conventional hydraulic entangling equipment such as may be found in, for example, U.S. Pat. No. 3,485,706 to Evans or U.S. Pat. No. 5,389,202 to Everhart, et al., the disclosures of which are hereby incorporated by reference.

In one embodiment, the base web may comprise a laminate containing two or more webs. For instance, the web may comprise a spunbonded/meltblown/spunbonded laminate, a spunbonded/meltblown laminate and the like.

For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of from about 60% to about 10% total bond area.

As discussed, when the finger wipe of the present invention is used to scrub or clean surfaces, in some embodiments, the cover layer 28 and/or pouch material 38 may include a texturized surface, such as the surface illustrated in the embodiments shown in FIGS. 3, 4, and 5. When used in dental applications, for instance, the texturized surface can facilitate removal of residue and film from the teeth and gums.

The manner in which a texturized surface is formed on a nonwoven web for use in the present invention can vary depending upon the particular application of the desired result. The substrate sections may be made from a nonwoven web that has been thermally point unbonded to form a plurality of tufts. As used herein, a substrate that has been "thermally point unbonded" refers to a substrate that includes raised unbonded areas or lightly bonded areas that are surrounded by bonded regions. For example, as shown in the figures, bumps or tufts are the unbonded or lightly bonded areas that form raised projections off the surface of the nonwoven web to provide the necessary texture.

The material used for the point unbonding process can vary depending upon the particular application. For instance, the material can be a single layer or can include multiple layers of material. For most applications, the total basis weight of the material should be at least 1 osy, and particularly from about 3 osy to about 9 osy. Higher basis weights are needed in order to produce tufts with an appropriate height.

Besides point unbonded materials, there are many other methods for creating texturized surfaces on base webs and many other texturized materials can be utilized.

Examples of known nonwoven, texturized materials, include rush transfer materials, flocked materials, wireformed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. No. 4,818,464 to Lau and U.S. Pat. No. 4,100,324 to Anderson, et al. Webs produced by the coform process are generally referred to as coform materials.

In one embodiment, the texturized material can be a loop material. As used herein, a loop material refers to a material that has a surface that is at least partially covered by looped bristles that can vary in height and stiffness depending upon the particular application. Further, the looped bristles can be sparsely spaced apart or can be densely packed together. The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

Liquid Impermeable Material Layers

Finger wipes according to the invention may include a liquid impermeable layer that is positioned interior of the wipe adjacent one or both of the sections. This liquid impermeable layer may be separate from the base web, or constitute a component of the base web. In the embodiment of FIG. 6 wherein the pouch 32 includes its own backing layer 40, such layer is liquid impermeable.

The liquid impermeable layer(s) can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the wipe to the finger, the use of such liquid- and vapor-impermeable barriers can sometimes result in a relatively uncomfortable level of humidity being maintained in the finger wipe. As such, in some embodiments, breathable, liquid-impermeable barriers are desired. As used herein, the term "breathable" means that the barrier or film is pervious to water vapor and gases. In other words, "breathable barriers" and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun, et al., which is incorporated herein in its entirety by reference. The breathable barrier of Braun, et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids that connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker, et al., which is incorporated herein by reference. The fabric material described in Junker, et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. It is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-Impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Liquid impermeable layers, as described above, can be used alone or incorporated into a laminate when used to construct various components of the finger wipe of the present invention. When incorporated into a laminate, the laminate can include various nonwoven webs in combination with the liquid impermeable layer. For instance, liquid impermeable laminates can be formed from many processes, such as, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate liquid impermeable layer of the present invention is a spunbond/meltblown/spunbond (SMS) and/or spunbond/meltblown (SM) material. An SMS material is described in U.S. Pat. No. 4,041,203 to Brock, et al. which is incorporated herein in its entirety by reference. Other SMS products and processes are described for example in U.S. Pat. No. 5,464,688 to Timmons, et al., U.S. Pat. No. 5,169,706 to Collier, et al. and U.S. Pat. No. 4,766,029 to Brock, et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

In some embodiments, any of the above layers and/or materials can also be dyed or colored so as to form a base web or liquid impermeable layer having a particular color. For example, in one embodiment, the liquid impermeable layer can be provided with a colored background.

Elastic Component

As described above, the finger wipes 10 may include one or more elastic components for providing the wipe with form-fitting properties. For example, one or both of the panel sections may be made of an elastic material, or include elastic components. In addition, the pouch material 38 may be elastomeric. The materials can contain elastic strands or sections uniformly or randomly distributed throughout the material. Alternatively, the elastic component can be an elastic film or an elastic nonwoven web.

In general, any material known in the art to possess elastomeric characteristics can be used in the present invention as an elastomeric component. Useful elastomeric materials can include, but are not limited to, films, foams, nonwoven materials, etc.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Amhem, Holland and now available from DSM of Sittard, Holland.

Another suitable material is a polyester block amide copolymer. Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck-bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, spunbond filaments or foams. A film, for example, can be formed by extruding a filled elastomeric polymer and subsequently stretching it to render it microporous.

In one embodiment, the elastic member can be a neck stretched bonded laminate. As used herein, a neck stretched bonded laminate is defined as a laminate made from the combination of a neck-bonded laminate and a stretch-bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch-bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger wipe having stretch characteristics in two directions and having a textured surface for cleaning the teeth and gums of a user.

Compositions and Additives

As mentioned, the composition containers 34 may hold any manner of desired composition to be applied by the wipes 10. In addition, the tubular structure 12 may also incorporate the same or another additive. Any material, chemical, or additive commonly applied by cotton ball, swabs, or gauzes, and so forth, can be applied with a wipe of the present invention. Examples of such additives can include, but are not limited to, medications, lotions, diaper rash ointments, alcohols, oral anesthetics, facial make-up removal agents, cleaning agents, polishing agents, and the like.

Certain compositions and additives are used when the finger wipe is intended as an oral cleaning device. Examples of such dental agents include, but are not limited to alginates, soluble calcium salts, phosphates, fluorides, such as sodium fluoride (NaF) or stannous fluoride (SnF2), and the like. Moreover, mint oils and mint oil mixtures can be applied to a finger wipe of the present invention. For instance, in one embodiment, peppermint oil can be applied to the finger wipe. Moreover, in another embodiment, a mint oil/ethanol mixture can be applied. Components of mint oil (e.g., menthol, carvone) can also be used. Additionally, various whitening agents can be applied to the finger wipe. Examples of whitening agents include peroxides and in situ sources of peroxide, such as carbamide peroxide.

Other additives and compositions can include, but are not limited to, flavoring agents, anti-microbial agents, preservatives, polishing agents, hemostatic agents, surfactants, etc. Examples of suitable flavoring agents include various sugars, breath freshening agents, and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a finger wipe of the present invention. The additives can be applied to the finger wipe as is or they can be encapsulated in order to preserve the additives and/or to provide the additive with time release properties.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A wipe, comprising:
a substrate having an application side defining an application surface, an opposite side, and two opposing ends;
a pouch configured on said application side of said substrate and generally located at an end of the wipe, said pouch having an access opening into an internal space of said pouch, said pouch formed from a material separate from said application side of said substrate and covering only a portion of said application side of said substrate so that said application surface comprises two separate materials, wherein said pouch is formed at least in part of an elastic material;
a composition delivered upon use of said wipe, said composition stored in a rupturable container inserted into said pouch through said access opening;
wherein with use of said wipe, said container within said pouch is ruptured and said composition is delivered through said pouch for application by said wipe; and
wherein said pouch is defined by a liquid permeable material attached to said application side of said substrate, said access opening defined between said liquid permeable material said substrate.

2. The wipe as in claim 1, wherein said wipe is configured as a tubular structure having an opening for insertion of one or more of a user's fingers, said substrate defining a side of said tubular structure.

3. The wipe as in claim 1, wherein said pouch comprises a separately formed structure having a backing layer attached to said application side of said substrate.

4. The wipe as in claim 1, wherein said substrate is a liquid impermeable material and said pouch is defined by a liquid permeable material, said liquid impermeable material defining a back surface of said pouch.

5. The wipe as in claim 1, wherein said container comprises a gel capsule having a size and shape so as to slide within said pouch.

6. The wipe as in claim 1, wherein said access opening comprises a closable seal configured to limit migration of said composition out of said access opening upon rupturing said rupturable container.

7. The wipe as in claim 6, wherein said substrate comprises a nonwoven material on said application side, said pouch comprising a hook material along said access opening that releasably secures to said nonwoven material.

8. The wipe as in claim 6, wherein said seal comprises a releasable adhesive.

9. The wipe as in claim 1, wherein said composition comprises a liquid composition.

10. The wipe as in claim 1, wherein said composition comprises a powder or granular composition that mixes with liquid upon use of said wipe.

11. The wipe as in claim 1, wherein said pouch has a size and configuration to hold at least two of said rupturable containers.

12. The wipe as in claim 1, wherein said rupturable container is stored within said pouch prior to use of said wipe.

13. The wipe as in claim 1, wherein said rupturable container is stored separate from said pouch prior to use of said wipe.

14. The wipe as in claim 1, further comprising a plurality of said rupturable containers filled with different said compositions, wherein any one or combination of said rupturable containers is insertable into said pouch for use of said wipe.

15. The wipe as in claim 1, wherein said pouch comprises a texturized outwardly facing surface.

16. The wipe as in claim 1, further comprising an additive incorporated with said substrate that is in addition to said composition delivered through said pouch.

17. A finger wipe, comprising:
a tubular structure having an open end for the insertion of an finger, an opposing closed end, and an outer surface defining an application surface;
a pouch configured on the outer surface of said tubular structure and generally located at the closed end of the tubular structure, said pouch having an access opening into an internal space of said pouch; said pouch formed from a material separate from said outer surface of said tubular structure and covering only a portion of said outer surface of said tubular structure so that said application surface comprises two separate materials, wherein said pouch is formed at least in part of an elastic material;
a composition delivered by said finger wipe upon use of said finger wipe, said composition stored in a container that is insertable into said pouch through said access opening, said pouch being permeable to said composition;
wherein with use of said finger wipe, said container releases said composition within said pouch and said composition is delivered through said pouch for application by said finger wipe; and
wherein said tubular structure comprises a liquid impermeable material, said pouch defined by a liquid permeable nonwoven material attached to said liquid impermeable material such that said liquid impermeable material defines a back surface of said pouch and prevents said composition from migrating through said tubular structure to the wearer's finger, said access opening defined between said liquid permeable nonwoven material said liquid impermeable material.

18. The finger wipe as in claim 17, wherein said container comprises a wall that ruptures upon application of pressure to said pouch.

19. The finger wipe as in claim 17, wherein said container comprises a gel capsule with said composition contained within said capsule.

20. The finger wipe as in claim 17, wherein said container comprises a wall that dissolves upon exposure to a liquid during use of said finger wipe.

21. The finger wipe as in claim 17, wherein said pouch comprises a separately formed structure having a liquid impermeable backing layer attached to said outer surface of said tubular structure.

22. The finger wipe as in claim 17, wherein said access opening comprises a closable seal configured to limit migration of said composition out of said access opening.

23. The finger wipe as in claim 17, wherein said pouch has a size and configuration to hold at least two of said containers.

24. The finger wipe as in claim 17, wherein said container is positioned within said pouch so as to be pressed by the user's finger or fingers against a surface to rupture said container.

25. The finger wipe as in claim 17, wherein said container is positioned within said pouch so as to be squeezed between a user's fingers to rupture said container.

26. A kit, comprising a plurality of said finger wipes as in claim 17 with a plurality of said containers tilled with the same or different said compositions, said finger wipes and compositions contained within a common package.

27. The finger wipe of claim 17, wherein the access opening is on the side of the pouch closest to the closed end of the tubular structure.

28. The finger wipe of claim 17, wherein the pouch is formed of an elastic nonwoven web.

29. The finger wipe of claim 1, wherein the pouch is formed of an elastic nonwoven web.

* * * * *